US00PP24328P2

(12) United States Plant Patent
Pierce

(10) Patent No.: US PP24,328 P2
(45) Date of Patent: Mar. 18, 2014

(54) *CALIBRACHOA* PLANT NAMED 'CBRZ0004'

(50) Latin Name: ***Calibrachoa* spp.**
Varietal Denomination: CBRZ0004

(75) Inventor: Robert O. Pierce, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 90 days.

(21) Appl. No.: 13/507,781

(22) Filed: Jul. 27, 2012

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — Susan McCormick Ewoldt
(74) *Attorney, Agent, or Firm* — Joshua L. Price

(57) ABSTRACT

A new *Calibrachoa* plant named 'CBRZ0004' particularly distinguished by the medium sized yellow flowers, is early to bloom, flowers continuously in the center of the plant and has a highly branched plant habit.

1 Drawing Sheet

Latin name of the genus and species of the plant claimed: *Calibrachoa* spp.

Varietal denomination: 'CBRZ0004'.

BACKGROUND OF THE NEW PLANT

The present invention comprises a new *Calibrachoa,* botanically known as *Calibrachoa* spp., and hereinafter referred to by the variety name 'CBRZ0004'.

'CBRZ0004' is a product of a planned breeding program. The new cultivar has medium sized yellow flowers, is early to bloom, flowers continuously in the center of the plant and has a highly branched plant habit.

'CBRZ0004' originated from a hybridization made in September 2007 in a greenhouse in Gilroy, Calif. USA. The female parent was an unpatented, proprietary plant designated '1808-1' with deep yellow flowers, darker green leaves and fewer flowers in the center of the plant when compared to 'CBRZ0004'.

The male parent of 'CBRZ0004' was an unpatented, proprietary plant identified as '1777-1' with deep medium yellow flowers, larger leaves, smaller diameter flowers and fewer branches when compared of 'CBRZ0004'. The seeds were sown in July 2008.

'CBRZ0004' was selected as one flowering plant within the progeny of the stated cross in the September 2008 in a greenhouse in Gilroy, Calif.

The first act of asexual reproduction of 'CBRZ0004' was accomplished when vegetative cuttings were propagated from the initial selection in September 2008 in a greenhouse in Gilroy, Calif.

BRIEF SUMMARY OF INVENTION

Horticultural examination of plants grown from cuttings of the plant initiated in September 2008, and continuing thereafter, has demonstrated that the combination of characteristics as herein disclosed for 'CBRZ0004' are firmly fixed and are retained through successive generations of asexual reproduction.

'CBRZ0004' has not been observed under all possible environmental conditions. The phenotype may vary significantly with variations in environment such as temperature, light intensity, and day length.

Plant Breeder's Rights for this cultivar were applied for in Canada on Nov. 1, 2011 (11-7411) and at Community Plant Variety Office on Jul. 20, 2012 (2012/1618). 'CBRZ0004' has not been made publicly available more than one year prior to the filing of this application.

The following traits have been repeatedly observed and are determined to be basic characteristics of the new variety. The combination of these characteristics distinguishes this *Calibrachoa* as a new and distinct variety.

BRIEF DESCRIPTION OF THE PHOTOGRAPHS

The accompanying photographic drawing shows typical flower and foliage characteristics of 'CBRZ0004' with colors being as true as possible with an illustration of this type.

Figure 1:
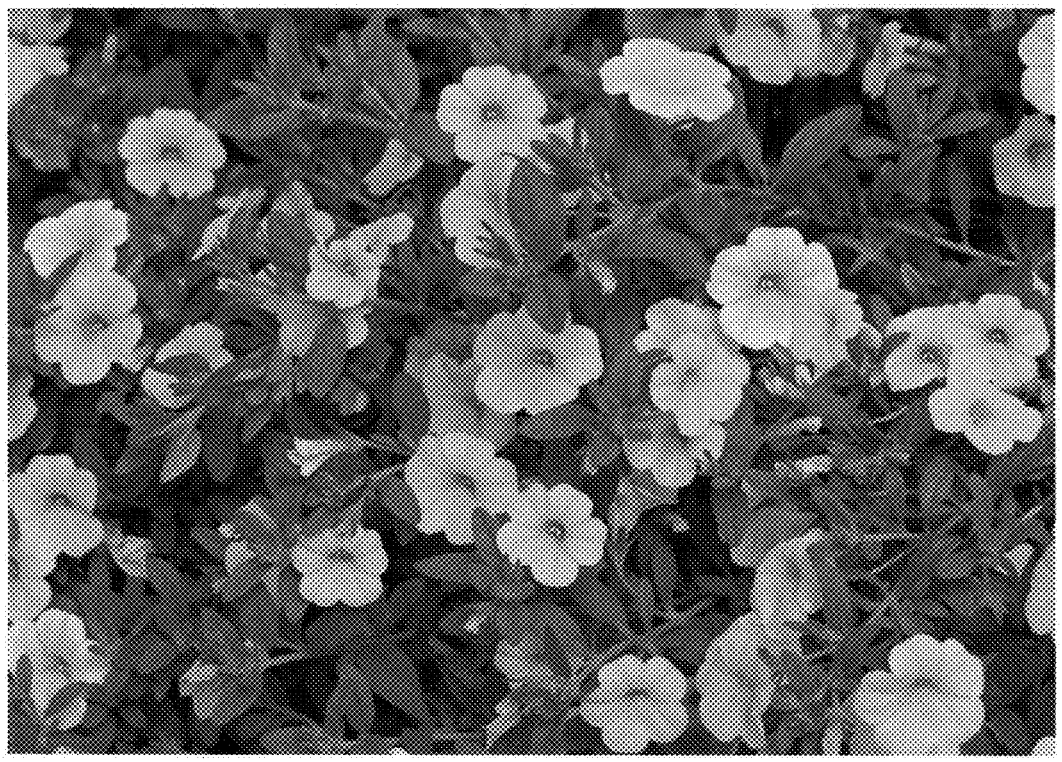
Figure 2:
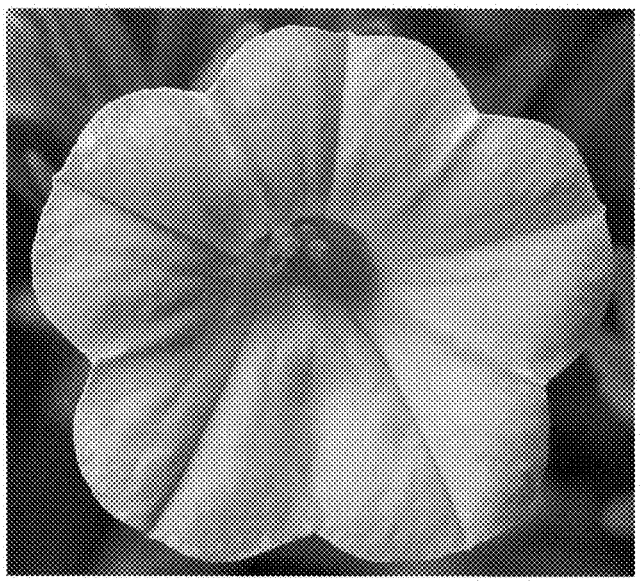

The photographic drawing shows in FIG. 1, a flowering plant of the new variety and in FIG. 2, a close-up a flower.

DETAILED BOTANICAL DESCRIPTION

The plant descriptions and measurements were taken in Gilroy, Calif. under natural light in May 2012. These plants were approximately 16-17 weeks old and were growing in 1 gallon pots in greenhouse trials. The plants used for the photographs were about 15 weeks old growing in Gilroy, Calif. and the photographs were taken in April 2011 in a greenhouse.

Color references are made to The Royal Horticultural Society Colour Chart (R.H.S.) 2001.

TABLE 1

DIFFERENCES BETWEEN THE NEW VARIETY 'CBRZ0004' AND A MOST SIMILAR VARIETY

| | 'CBRZ0004' | 'Cal Depyel' (U.S. Plant Pat. No. 17,883) |
|---|---|---|
| Flower size: | Larger | Smaller |
| Center flowering habit: | Has more flowers | Fewer flowers |
| Flower timing: | Earlier | Later |

Plant:

*Form, growth and habit.*—Initially mounding, then more spreading and decumbent, pinching enhances the number of branches.

*Plant height.*—8-10.0 cm.

*Plant height (inflorescence included).*—10-12.0 cm.

*Plant width.*—About 55.0 cm.

Roots:

*Number of days to initiate and produce a rooted cutting.*—25-28 days at about 22 degrees C.

*Type.*—Fine, fibrous, free branching.

*Color.*—RHS N155B but whiter.

Foliage:

*Arrangement.*—Alternate, simple.

*Immature, leaf color, upper surface.*—Slightly mottled with RHS 137A and RHS 137B.

*Lower surface.*—Closest to RHS 147B but lighter.

*Mature, leaf color, upper surface.*—Slightly mottled with RHS 137A and RHS 137B.

*Lower surface.*—Closest to RHS 147b but lighter.

*Length.*—3.4-3.7 cm.

*Width.*—1.5 cm.

*Shape.*—Elliptical.

*Base shape.*—Acuminate.

*Apex shape.*—Obtuse.

*Margin.*—Entire.

*Texture, upper surface.*—Glandular hairs.

*Lower surface.*—Glandular hairs on mid-veins only.

*Color of veins, upper surface.*—RHS 138B.

*Color of veins, lower surface.*—RHS 138B.

*Pattern of veining.*—Pinnate.

*Petiole color.*—RHS 138B.

*Length.*—0.3-0.4 cm.

*Diameter.*—0.15 cm.

*Texture.*—Glandular hairs.

Stem:

*Quantity of main branches per plant.*—6-9.

*Color of stem.*—Lighter than RHS 146B.

*Length of stem.*—23-27.0 cm.

*Diameter.*—0.15-0.2 cm.

*Length of internodes.*—1.1-1.5 cm.

*Texture.*—Glandular hairs.

*Color of pedicel.*—Lighter than RHS 146B.

*Length of pedicel.*—2.5-2.7 cm.

*Diameter of pedicel.*—0.1 cm.

*Texture of pedicel.*—Heavily covered with glandular hairs.

Inflorescence:

*Type.*—Flowers solitary in upper leaf axis; flowers face mainly horizontally, mostly 5-fused lobes forming a funnel form flower. Continuous flowering and good center flowering throughout the Summer.

*Quantity of inflorescences per plant.*—150-200.

*Lastingness of individual blooms on the plant.*—About 7-9 days.

*Fragrance.*—None.

Bud (just when opening/showing color):

*Color.*—Closest to RHS 151 but lighter.

*Length.*—2.3-2.5 cm.

*Width.*—0.5-0.6 cm.

*Shape.*—Oblong.

Corolla:

*Immature inflorescence.*—Flower horizontal diameter: 2.3-3.0 cm. Color petals, upper surface: Closest to RHS 9A. Lower surface: Closest to RHS 10B.

*Mature inflorescence.*—Flower horizontal diameter: 3.5-3.7 cm. Flower height (vertical): 2.3 cm. Color petals, upper surface: RHS 9B becoming between RHS 9B and RHS 9C with veining of RHS 1B. Lower surface: RHS 10B to RHS 10C. Apex shape: Slightly mucronulate. Margin: Entire. Waviness of petals: Slightly recurving. Petal lobation: Moderate. Petal texture: Papillose on both sides. Corolla tube color inside: RHS 10B to RHS 10C with mid-veins of about RHS 144B. Color outside: RHS 9A. Corolla tube length: 1.5 cm. Corolla texture, outside: Glandular hairs; hirsute. Texture inside: Glandular hairs; hirsute.

Calyx:

*Quantity of sepals.*—5, fused at the base.

*Color, upper surface.*—RHS 144B with about RHS 146A apex.

*Lower surface.*—Closest to RHS 146C with almost RHS 146A apex.

*Length.*—1.5-1.6 cm.

*Width.*—0.25 cm.

*Shape.*—Lanceolate.

*Apex shape.*—Acute.

*Margins.*—Entire.

*Texture, upper surface.*—Glandular hairs.

*Lower surface.*—Glandular hairs.

Reproductive organs:

*Gynoecium.*—Pistil: 1. Length: 1.1 cm. Style color: RHS 155C but more green. Style length: 0.7-0.8 cm. Stigma color: RHS 145A. Stigma shape: Flattened capitate. Ovary color: RHS 145C. Ovary length: 0.2 cm. Ovary diameter: 0.175 cm.

*Androecium.*—Stamens: 1. Color of filaments: RHS 1D. Length filaments: 0.7-1.1 cm. Anther color: RHS 4D. Anther length: 0.15 cm. Anther shape: Elliptical. Color of pollen: RHS 14D. Pollen amount: Moderate.

*Fertility/seed set.*—Has not been determined to date.

*Disease/pest resistance.*—Has not been determined to date.

What is claimed is:

1. A new and distinct variety of *Calibrachoa* plant named 'CBRZ0004' substantially as illustrated and described herein.

* * * * *